United States Patent [19]
Baker et al.

[11] Patent Number: 5,981,529
[45] Date of Patent: *Nov. 9, 1999

[54] SUBSTITUTED INDOLYLPROPYL-PIPERAZINE DERIVATIVES AS 5-HT$_{1D}\alpha$ AGONISTS

[75] Inventors: Raymond Baker, Uley; Mark Stuart Chambers, Puckeridge; Sarah Christine Hobbs, Great Dunmow; Angus Murray MacLeod, Bishops Stortford; Austin John Reeve, Great Dunmow; Francine Sternfeld, London; Leslie Joseph Street, Harlow, all of United Kingdom

[73] Assignee: Merck Sharp & Dohme Limited, Hoddesdon, United Kingdom

[*] Notice: This patent is subject to a terminal disclaimer.

[21] Appl. No.: 09/043,440

[22] PCT Filed: Sep. 19, 1996

[86] PCT No.: PCT/GB96/02309

§ 371 Date: Mar. 18, 1998

§ 102(e) Date: Mar. 18, 1998

[87] PCT Pub. No.: WO97/11695

PCT Pub. Date: Apr. 3, 1997

[30] Foreign Application Priority Data

Jan. 15, 1995 [GB] United Kingdom ............... 9523441
Sep. 28, 1995 [GB] United Kingdom ............... 9519786

[51] Int. Cl.$^6$ .............. A61K 31/495; C07D 403/14; C07D 413/14

[52] U.S. Cl. .................. 514/253; 544/366; 544/369; 544/370

[58] Field of Search .................. 544/366, 369, 544/370; 514/253

[56] References Cited

U.S. PATENT DOCUMENTS

| | | | |
|---|---|---|---|
| 5,807,857 | 9/1998 | Castro Pineiro et al. | 514/253 |
| 5,808,064 | 9/1998 | Chen et al. | 544/132 |

FOREIGN PATENT DOCUMENTS

| | | |
|---|---|---|
| 0 548 813 A1 | 6/1993 | European Pat. Off. . |
| 94/02477 | 2/1994 | WIPO . |
| 95/32196 | 11/1995 | WIPO . |
| 96/16056 | 5/1996 | WIPO . |
| 9706159 | 2/1997 | WIPO . |

*Primary Examiner*—Emily Bernhardt
*Attorney, Agent, or Firm*—James L. McGinnis; David L. Rose; Philippe L. Durette

[57] ABSTRACT

A class of 1-[3-(1H-indol-3-yl)propyl]-4-(2-phenylethyl) piperazine derivatives, substituted at the 5-position of the indole nucleus by a five-membered heteroaromatic moiety, on one or other of the ethylene carbon atoms of the phenethyl moiety by halogen, trifluoromethyl, alkyl, hydroxyalkyl or alkoxyalkyl, and optionally on the phenyl ring of the phenethyl moiety by halogen, trifluoromethyl, alkoxy or an oxazolidinone group and optionally by one or two further substituents, are selective agonists of 5-HT$_1$-like receptors, being potent agonists of the human 5-HT$_{1D}\alpha$ receptor subtype whilst possessing at least a 10-fold selective affinity for the 5-HT$_{1D}\alpha$ receptor subtype relative to the 5-HT$_{1D}\beta$ subtype; they are therefore useful in the treatment and/or prevention of clinical conditions, in particular migraine and associated disorders, for which a subtype-selective agonist of 5-HT$_{1D}$ receptors is indicated, whilst eliciting fewer side-effects, notably adverse cardiovascular events, than those associated with non-subtype-selective 5-HT$_{1D}$ receptor agonists.

8 Claims, No Drawings

SUBSTITUTED INDOLYLPROPYL-PIPERAZINE DERIVATIVES AS 5-HT$_{1D}$α AGONISTS

The present invention relates to a class of substituted piperazine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example. F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D\alpha}$ and 5-HT$_{1D\beta}$ receptor subtypes (cf. WO-A-91/17174. Table 1). and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf G. W. Rebeck et al., *Proc. Natl. Acad. Sci. USA*, 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent application 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the substituted piperazine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the alkoxypyridine or alkoxypyrimidine substituent with a substituted phenylethyl moiety; nor is there any suggestion therein that the range of substituents specified at the 5-position of the indole moiety might be replaced by an imidazole or triazole ring.

Moreover, nowhere in the prior art mentioned above is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

The compounds according to the present invention are subtype-selective 5-HT$_{1D}$ receptor agonists having a human 5-HT$_{1D\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D\alpha}$ receptor subtype relative to the 5-HT$_{1D\beta}$ subtype. Moreover, the compounds in accordance with this invention possess interesting properties in terms of their efficacy and/or bioavailability.

The present invention provides a compound of formula I, or a salt or prodrug thereof:

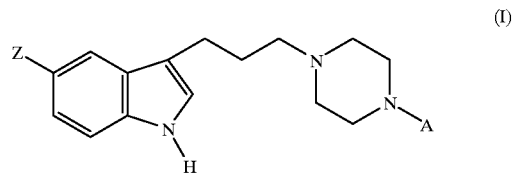

(I)

wherein

A represents a group of formula (i) or (ii):

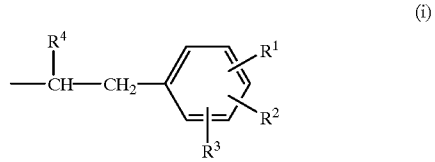

(i)

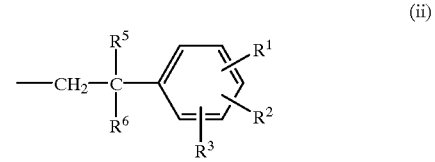

(ii)

in which

R$^1$ represents hydrogen, halogen, trifluoromethyl, C$_{1-6}$ alkoxy or a group of formula (a):

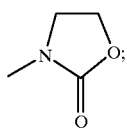

(a)

$R^2$ and $R^3$ independently represent hydrogen, halogen, trifluoromethyl or $C_{1-6}$ alkoxy;

$R^4$ represents $C_{1-6}$ alkyl, hydroxy($C_{1-6}$)alkyl or $C_{1-6}$ alkoxy($C_{1-6}$)alkyl;

$R^5$ represents halogen, trifluoromethyl, $C_{1-6}$ alkyl, hydroxy($C_{1-6}$)alkyl or $C_{1-6}$ alkoxy($C_{1-6}$)alkyl; and $R^6$ represents hydrogen or halogen;

Z represents a group of formula (Za), (Zb) or (Zc):

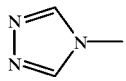

(Za)

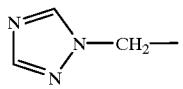

(Zb)

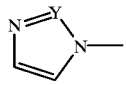

(Zc)

in which

Y represents nitrogen or C—$R^7$; and $R^7$ represents hydrogen or $C_{1-6}$ alkyl.

The present invention also provides compounds of formula I above, and salts and prodrugs thereof, wherein A represents a group of formula (i) or (ii) in which $R^5$ represents $C_{1-6}$alkyl, hydroxy($C_{1-6}$)alkyl or $C_{1-6}$ alkoxy($C_{1-6}$)alkyl, and $R^6$ represents hydrogen; and Z represents a group of formula (Za) as defined above.

The compounds in accordance with the present invention are encompassed within the generic scope of co-pending International Patent Application No. PCT/GB95/01129, published as WO 95/32196 on Nov. 30, 1995. There is, however, no specific disclosure therein of compounds corresponding to those of formula I above wherein A and Z are as defined above.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy" are to be construed accordingly.

The term "halogen" as used herein includes fluorine, chlorine, bromine and iodine, especially fluorine or chlorine, and particularly fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs,* ed. H. Bundgaard, Elsevier, 1985.

The compounds according to the invention have at least one asymmetric centre, and they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I above, the moiety $R^1$ suitably represents hydrogen, fluoro, trifluoromethyl, methoxy or a group of formula (a) as defined above. Particular values of $R^1$ include hydrogen and fluoro.

Suitably, $R^2$ and $R^3$ independently represent hydrogen, fluoro, trifluoromethyl or methoxy, in particular hydrogen or fluoro. Suitably, one or both of $R^2$ and $R^3$ represents hydrogen.

Particular values of $R^4$ include methyl, hydroxymethyl and methoxymethyl.

Particular values of $R^5$ include fluoro, trifluoromethyl, methyl, hydroxymethyl and methoxymethyl.

Suitably, $R^6$ represents hydrogen or fluoro, especially hydrogen.

Suitably, the variable Y in formula (Zc) represents nitrogen, CH or C-methyl.

Suitably, $R^7$ represents hydrogen or methyl, especially hydrogen.

A particular sub-class of compounds according to the invention is represented by the compounds of formula II, and salts and prodrugs thereof:

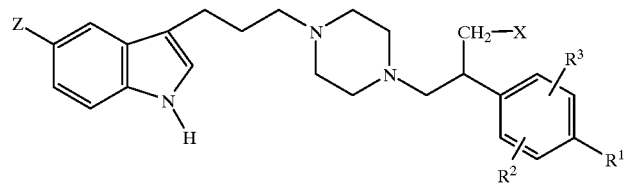

(II)

wherein Z, $R^1$, $R^2$ and $R^3$ are as defined above; and

X represents hydrogen, hydroxy or methoxy.

Particular values of $R^1$ in relation to formula II above include hydrogen and fluoro.

In one embodiment of the compounds of formula II above, $R^2$ is hydrogen and $R^3$ is other than hydrogen.

In another embodiment of the compounds of formula II above, $R^2$ and $R^3$ are both hydrogen.

In a typical aspect of the compounds of formula II above, Z represents a group of formula (Za) as defined above.

In another aspect of the compounds of formula II above, Z represents a group of formula (Zb) as defined above.

Suitably, X is hydrogen.

Specific compounds within the scope of the present invention include:

1-[3-(5-(1,2,4-triazol-4-yl)-1H-indol-3-yl)propyl]-4-(3-hydroxy-2-phenylpropyl)piperazine;
1-[3-(5-(1,2,4-triazol-4-yl)-1H-indol-3-yl)propyl]-4-(3-methoxy-2-phenylpropyl)piperazine;
1-[3-(5-(1,2,4-triazol-4-yl)-1H-indol-3-yl)propyl]-4-[2-(4-fluorophenyl)-3-hydroxypropyl]piperazine;
1-[3-(5-(1,2,4-triazol-4-yl)-1H-indol-3-yl)propyl]-4-[1-(4-fluorophenyl)prop-2-yl]piperazine;
1-[3-(5-(1,2,4-triazol-4-yl)-1H-indol-3-yl)propyl]-4-[2-(4-fluorophenyl)propyl]piperazine;
1-[3-(5-(1,2,4-triazol-4-yl)-1H-indol-3-yl)propyl]-4-[1-(4-fluorophenyl)-3-hydroxyprop-2-yl]piperazine;
1-[3-(5-(1,2,4-triazol-4-yl)-1H-indol-3-yl)propyl]-4-[1-(4-fluorophenyl)-3-methoxyprop-2-yl]piperazine;
1-[3-(5-(imidazol-1-yl)-1H-indol-3-yl)propyl]-4-(2-phenylpropyl)piperazine;
1-[3-(5-(imidazol-1-yl)-1H-indol-3-yl)propyl]-4-[2-(4-fluorophenyl)propyl]piperazine;
1-[3-(5-(1,2,4-triazol-1-ylmethyl)-1H-indol-3-yl)propyl]-4-[2-(4-fluorophenyl)propyl]piperazine;
1-[3-(5-(1,2,4-triazol-4-yl)-1H-indol-3-yl)propyl]-4-[2-(3-fluorophenyl)-3-methoxypropyl]piperazine;
1-[3-(5-(1,2,3-triazol-1-yl)-1H-indol-3-yl)propyl]-4-[2-(4-fluorophenyl)propyl]piperazine;
1-[3-(5-(1,2,4-triazol-4-yl)-1H-indol-3-yl)propyl]-4-[2-(3-fluoropheny 3,3,3-trifluoropropyl]piperazine;
1-[3-(5-(1,2,4-triazol-4-yl)-1H-indol-3-yl)propyl]-4-(2,2-difluoro-2-phenylethyl)piperazine;
1-[3-(5-(1,2,4-triazol-4-yl)-1H-indol-3-yl)propyl]-4-[2-(3-fluorophenyl)-3-hydroxypropyl]piperazine;
1-[3-(5-(1,2,4-triazol-4-yl)-1H-indol-3-yl)propyl]-4-(2-phenylpropyl)piperazine;
1-[3-(5-(2-methylimidazol-1-yl)-1H-indol-3-yl)propyl]-4-[2-(4-fluorophenyl)propyl]piperazine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories: for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil s sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises reacting a compound of formula III with a compound of formula IV:

(III)

(IV)

$L^1$—A wherein A and Z are as defined above, and $L^1$ represents a suitable leaving group.

The leaving group $L^1$ is suitably a halogen atom, e.g. chlorine or bromine, or an alkylsulphonyloxy or arylsulphonyloxy group, e.g. methanesulphonyloxy (mesyloxy) or p-toluenesulphonyloxy (tosyloxy).

The reaction between compounds III and IV is conveniently effected by stirring the reactants under basic conditions in a suitable solvent, for example triethylamine in N,N-dimethylformamide or isopropanol, typically in the presence of sodium iodide.

In another procedure, the compounds according to the invention wherein A represents a group of formula (i) or (ii) as defined above may be prepared by a process which comprises reacting a compound of formula III as defined above with a compound of formula VA or VB respectively:

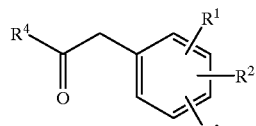
(VA)

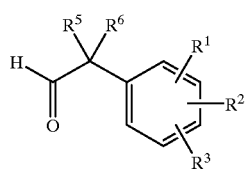
(VB)

wherein $R^1$, $R^2$, $R^3$, $R^4$, $R^5$ and $R^6$ are as defined above; in the presence of a reducing agent.

A suitable reducing agent for effecting this process is sodium cyanoborohydride, and the reaction is conveniently carried out in methanol or methanol/acetic acid at room temperature.

In a further procedure, the compounds according to the invention wherein A represents a group of formula (ii) as defined above may be prepared by a process which comprises reacting a compound of formula III as defined above with a carboxylic acid derivative of formula VI:

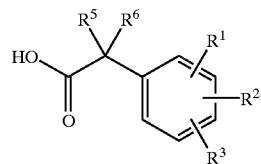
(VI)

wherein $R^1$, $R^2$, $R^3$, $R^5$ and $R^6$ are as defined above; in the presence of a condensing agent; followed by treatment with a reducing agent such as diisobutylaluminium hydride or borane-tetrahydrofuran.

Condensing agents suitable for use in conjunction with the above process comprise 1-(3-dimethylaminopropyl)-3-ethylcarbodiimide and 1-hydroxybenzotriazole hydrate, or bis(2-oxo-3-oxazolidinyl)phosphinic chloride in triethylamine.

The compounds of formula III above may be prepared by a process which comprises reacting a compound of formula VII:

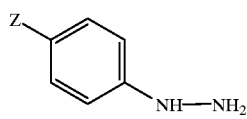
(VII)

wherein Z is as defined above; with a compound of formula VIII, or a carbonyl-protected form thereof:

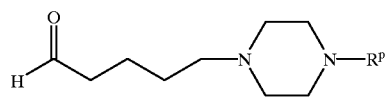
(VIII)

wherein $R^P$ represents an amino-protecting group; with subsequent removal of the amino-protecting group $R^P$.

The reaction between compounds VII and VIII, which is an example of the well-known Fischer indole synthesis, is suitably carried out by heating the reagents together under mildly acidic conditions, e.g. 4% sulphuric acid at reflux.

Suitable carbonyl-protected forms of the compounds of formula VIII include the dimethyl acetal derivatives.

The protecting group $R^P$ in the compounds of formula VIII is suitably a carbamoyl moiety such as tert-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds VII and VIII may be carried out in a single step, or may proceed via an initial non-cyclising step at a lower temperature to give an intermediate of formula IX:

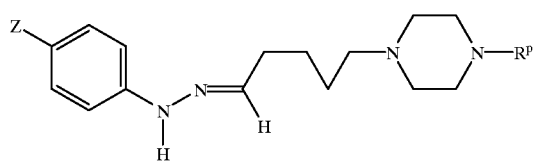
(IX)

wherein Z and $R^P$ are as defined above; followed by cyclisation using a suitable reagent, e.g. a polyphosphate ester.

The intermediates of formula VIII, or carbonyl-protected forms thereof, may be prepared by reacting a compound of formula X, or a carbonyl-protected form thereof, with a compound of formula XI:

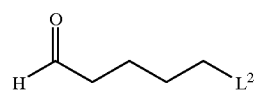
(X)

(XI)

wherein $R^P$ is as defined above, and $L^2$ represents a suitable leaving group.

The leaving group $L^2$ is suitably a halogen atom, e.g. chlorine or bromine.

Where $L^2$ represents a halogen atom, the reaction between compounds X and XI is conveniently effected by stirring the reactants under basic conditions in a suitable solvent, for example sodium carbonate or potassium carbonate in 1,2-dimethoxyethane or N,N-dimethyl-formamide, or triethylamine in tetrahydrofuran or acetonitrile, optionally in the presence of sodium iodide.

The compounds according to the invention may alternatively be prepared by a process which comprises reacting the appropriate compound of formula VII as defined above with a compound of formula XII, or a carbonyl-protected form thereof:

(XII)

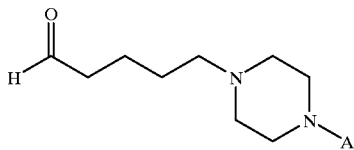

wherein A is as defined above; under conditions analogous to those described above for the reaction between compounds VII and VIII.

As for the compounds of formula VIII, suitable carbonyl-protected forms of the compounds of formula XII include the dimethyl acetal derivatives.

As with that between compounds VII and VIII, the Fischer reaction between compounds VII and XII may be carried out in a single step, or may proceed via an initial non-cyclising step at a lower temperature to give an intermediate of formula XIII:

(XIII)

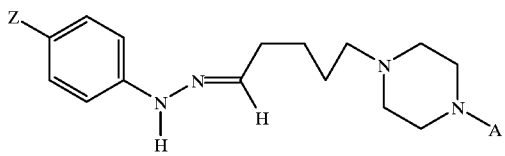

wherein Z and A are as defined above; followed by cyclisation using a suitable reagent, e.g. a polyphosphate ester.

The intermediates of formula XII, or carbonyl-protected forms thereof, may be prepared by reacting a compound of formula X as defined above, or a carbonyl-protected form thereof, with a compound of formula XIV:

(XIV)

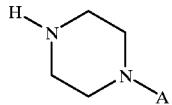

wherein A is as defined above; under conditions analogous to those described above for the reaction between compounds X and XI.

In an alternative procedure, the compounds of formula III above may be prepared by a process which comprises reacting a compound of formula XI as defined above with a compound of formula XV:

(XV)

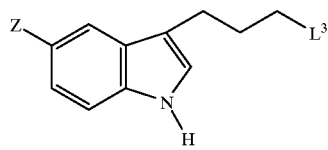

wherein Z is as defined above, and $L^3$ represents a suitable leaving group; followed by removal of the amino-protecting group $R^P$.

Similarly, the compounds of formula I as defined above may be prepared by a process which comprises reacting a compound of formula XIV as defined above with a compound of formula XV as defined above.

The leaving group $L^3$ is suitably an alkylsulphonyloxy or arylsulphonyloxy group, e.g. methanesulphonyloxy (mesyloxy) or p-toluenesulphonyloxy (tosyloxy).

Where $L^3$ represents an alkylsulphonyloxy or arylsulphonyloxy group, the reaction between compound XV and compound XI or XIV is conveniently carried out in a suitable solvent such as 1,2-dimethoxyethane or isopropyl alcohol, typically in the presence of a base such as sodium carbonate or potassium carbonate, optionally with the addition of sodium iodide.

In one representative approach, the compounds of formula XV wherein $L^3$ represents a mesyloxy or tosyloxy group may be prepared by the sequence of steps illustrated in the following reaction scheme (cf. Larock and Yum, *J. Am. Chem. Soc.*, 1991, 113, 6689):

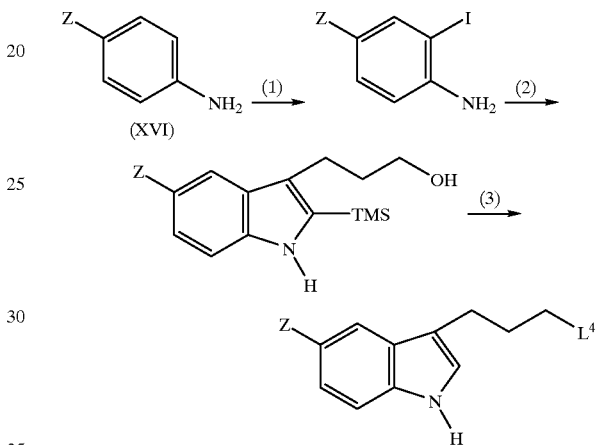

wherein Z is as defined above, $L^4$ represents mesyloxy or tosyloxy, and TMS is an abbreviation for trimethylsilyl.

In Step 1 of the reaction scheme, the aniline derivative XVI is treated with iodine monochloride, advantageously in methanol in the presence of a base such as calcium carbonate, in order to introduce an iodine atom ortho to the amine moiety. Step 2 involves a palladium-mediated coupling reaction with the protected acetylene derivative TMS—C≡C—(CH$_2$)$_3$—OH, typically using palladium acetate and triphenylphosphine in the presence of lithium chloride and sodium carbonate, suitably in N,N-dimethylformamide at an elevated temperature. This is followed in Step 3 by removal of the TMS moiety, ideally in refluxing methanolic hydrochloric acid: followed in turn by mesylation or tosylation, suitably by using mesyl chloride or tosyl chloride respectively in pyridine.

In another representative approach, the compounds of formula XV wherein $L^3$ represents a mesyloxy or tosyloxy group may be prepared by reacting 3,4-dihydro-2H-pyran with the appropriate compound of formula VII as defined above or a salt thereof, under a variant of the Fischer reaction conditions as described above for the reaction between compounds VII and VIII; followed by mesylation or tosylation of the 3-hydroxypropylindole derivative thereby obtained, typically by treatment with mesyl chloride or tosyl chloride under standard conditions.

The Fischer reaction with 3,4-dihydro-2H-pyran is suitably brought about by heating the appropriate hydrazine derivative VII or an acid addition salt thereof, typically the hydrochloride salt, in an inert solvent such as dioxan, advantageously in the presence of a mineral acid such as hydrochloric acid or a Lewis acid such as zinc chloride, at the reflux temperature of the solvent.

In a yet further procedure, the compounds of formula III above may be prepared by a process which comprises reducing a compound of formula XVII:

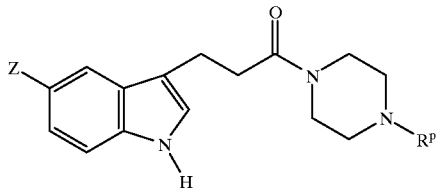

(XVII)

wherein Z and $R^P$ are as defined above, with subsequent removal of the amino-protecting group $R^P$.

Similarly, the compounds according to the invention may be prepared by a process which comprises reducing a compound of formula XVIII:

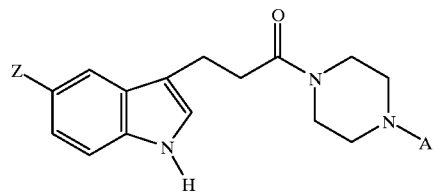

(XVIII)

wherein Z and A are as defined above.

The reduction of compound XVII or compound XVIII is conveniently effected by treating the appropriate compound with a reducing agent such as lithium aluminium hydride in an appropriate solvent, e.g. diethyl ether or tetrahydrofuran, or mixtures thereof.

The compounds of formulae XVII and XII above may suitably be prepared by reacting the appropriate compound of formula XI or XIV with a compound of formula XIX:

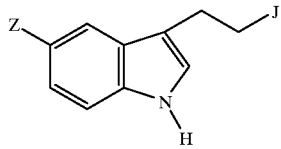

(XIX)

wherein Z is as defined above, and J represents a reactive carboxylate moiety.

Suitable values for the reactive carboxylate moiety J include esters for example $C_{1-4}$ alkyl esters: acid anhydrides, for example mixed anhydrides with $C_{1-4}$ alkanoic acids: acid halides, for example acid chlorides; and acylimidazoles.

By way of example, the intermediates of formula XIX above wherein J is an acid chloride moiety may be prepared by treating the corresponding carboxylic acid derivative with thionyl chloride in toluene. Similarly, the intermediates of formula XIX wherein J is an acylimidazole moiety may be prepared by treating the corresponding carboxylic acid derivative with 1,1'-carbonyldiimidazole. Alternatively, the reactive carboxylate moiety J may be obtained by treating the corresponding compound wherein J is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula XI or XIV.

In a still further procedure, the compounds of formula I above wherein $R^4$ or $R^5$ represents hydroxy($C_{1-6}$)alkyl may be prepared by a process which comprises reducing a compound of formula XX:

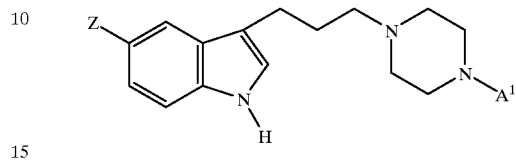

(XX)

wherein Z is as defined above, and $A^1$ represents a group of formula (iii) or (iv):

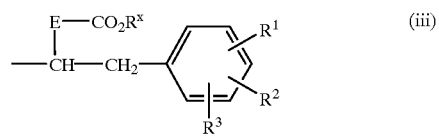

(iii)

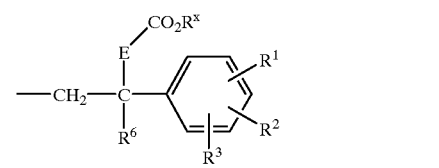

(iv)

in which E represents a chemical bond or a $C_{1-5}$ alkylene chain, $R^x$ represents $C_{1-6}$ alkyl, and $R^1$, $R^2$, $R^3$ and $R^6$ are as defined above.

The reduction of the ester functionality in compound XX may conveniently be effected by treatment with a reducing agent such as lithium aluminium hydride, typically in a solvent such as diethyl ether or tetrahydrofuran, or mixtures thereof.

The hydrazine derivatives of formula TII above can be prepared by the methods described in EP-A-0497512 and WO 94/03446, as also can the aniline derivatives of formula XVI.

Where they are not commercially available, the starting materials of formula IV, VA, VB, VI, X, XI, XIV, XIX and XX may be prepared by methods analogous to those described in the accompanying Examples, or by standard procedures well known from the art.

It will be understood that any compound of formula I initially obtained from any one of the above processes may, where appropriate, subsequently be elaborated into a further compound of formula I by techniques known from the art. For example, a compound of formula I wherein $R^4$ or $R^5$ is hydroxy($C_{1-6}$)alkyl initially obtained may be treated with mesyl chloride under standard conditions to obtain the corresponding mesylate, which in turn may be converted into the desired compound of formula I wherein $R^4$ or $R^5$ represents $C_{1-6}$ alkoxy($C_{1-6}$)alkyl by reaction with the appropriate $C_{1-6}$ alkoxide salt, for example sodium methoxide, typically in methanol/tetrahydrofuran with heating under sealed tube conditions.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the $5\text{-HT}_{1D\alpha}$ receptor subtype, inhibit forskolin-stimulated adenylyl cyclase activity, and stimulate [$^{35}$S]-GTPγS binding to membranes from clonal cell lines expressing human cloned receptors.

$5\text{-HT}_{1D\alpha}/5\text{-HT}_{1D\beta}$ Radioligand Binding

Chinese hamster ovary (CHO) clonal cell lines expressing the human $5\text{-HT}_{1D\alpha}$ and $5\text{-HT}_{1D\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48.000 g, 4° C. for 11 min and the pellet resuspended, in assay buffer (composition in mM: Tris-HCl 50, pargyline 0.01, $CaCl_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Walac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the $5\text{-HT}_{1D\alpha}$ receptor subtype obtained for the compounds of the accompanying Examples were below 50 nM in each case. Furthermore, the compounds of the accompanying Examples were all found to possess a selective affinity for the $5\text{-HT}_{1D\alpha}$ receptor subtype of at least 10-fold relative to the $5\text{-HT}_{1D\beta}$ subtype.

$5\text{-HT}_{1D\alpha}/5\text{-HT}_{1D\beta}$ Adenylyl Cyclase Assay

Studies were performed essentially as described in *J. Pharmacol. Exp. Ther.*, 1986, 238, 248. CHO clonal cell lines expressing the human cloned $5\text{-HT}_{1D\alpha}$ and $5\text{-HT}_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μl, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM $MgCl_2$, 1 mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the $5\text{-HT}_{1D\alpha}$ receptor obtained for the compounds of the accompanying Examples were below 500 nM in each case. Moreover, the compounds of the accompanying Examples which were tested were all found to possess at least a 10-fold selectivity for the $5\text{-HT}_{1D\alpha}$ receptor subtype relative to the $5\text{-HT}_{1D\beta}$ subtype.

$5\text{-HT}_{1D\alpha}/5\text{-HT}_{1D\beta}$ GTPγS Binding

Studies were performed essentially as described in *Br. J. Pharmacol.*, 1993, 109, 1120. CHO clonal cell lines expressing the human cloned $5\text{-HT}_{1D\alpha}$ and $5\text{-HT}_{1D\beta}$ receptors were harvested in PBS and homogenised using a Kinematica polytron in ice cold 20 mM HEPES containing 10 mM EDTA, pH 7.4 at room temperature. The membranes were then centrifuged at 40.000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, $MgCl_2$ 10, pargyline 0.01; ascorbate 0.1%; pH 7.4 at room temperature) at a concentration of 40 μg protein/ml for the $5\text{-HT}_{1D\alpha}$ receptor transfected cells and 40–50 μg protein/ml for the $5\text{-HT}_{1D\beta}$ receptor transfected cells. The membrane suspension was then incubated, in a volume of 1 ml, with GDP (100 μM for $5\text{-HT}_{1D\alpha}$ receptor transfected cells, 30 μM for the $5\text{-HT}_{1D\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect)

and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

EXAMPLE 1

(±)-1-[3-(5-(1,2,4-Triazol-4-yl)-1H-indol-3-yl) propyl]-4-(3-hydroxy-2-phenylpropyl)piperazine. 1.6 Hydrogen Oxalate. 0.4 Diethyl etherate 1. Intermediate 1: 3-[5-(1,2,4-Triazol-4-yl)-1H-indol-3-yl)propan-1-ol a) 4-(1,2,4-Triazol-4-yl)phenylhydrazine Prepared as described in WO 94/03446, Example 1.

b) 3-[5-(1,2,4-Triazol-4-yl)-1H-indol-3-yl]propan-1-ol

A solution of 4-(1,2,4-triazol-4-yl)phenylhydrazine (25 g, 143 mmol) in dioxan (250 ml) was treated with dihydropyran (24 g, 286 mmol) followed by 1M hydrochloric acid (150 ml) and heated at reflux for 18 hours. The reaction mixture was evaporated with toluene then reevaporated. Inorganic solids were removed by treating the residue with a mixture of methanol and acetonitrile. The mother liquors were purified by column chromatography on silica using dichloromethane:methanol (9:1→4:1) as the eluant. The compound was recrystallised from acetonitrile to afford the title compound as a white solid (10.24 g, 30%), mp 205–207° C. δ(360 MHz, $d_6$-DMSO) 1.81 (2H, quintet, J=7 Hz, $CH_2$), 2.75 (2H, t, J=8 Hz, $CH_2$), 3.46 (2H, dt, $J_1$=6 Hz, $J_2$=5 Hz, $CH_2$), 4.43 (1H, t, J=5 Hz, OH), 7.26 (1H, d, J=2 Hz, Ar-H), 7.29 (1H, dd, $J_1$=9 Hz, $J_2$=2 Hz, Ar-H), 7.47 (1H, d, J=9 Hz, Ar-H), 7.77 (1H, d, J=2 Hz, Ar-H), 9.01 (2H, s, Triazole-H), 11.05 (1H, br s, indole NH). MS, $CI^+$, m/z for $(M+H)^+$=243.

2. Intermediate 2: (±)-1-tert-Butyloxycarbonyl-4-(3-hydroxy-2-phenylpropyl)piperazine a) (±)-Methyl 2-(phenyl)-3-[4-(tert-butyloxycarbonyl)piperazine-1-yl]propionate Methyl 2-(phenyl)propenoate was prepared using the procedures described by Howard, A. S. et al. in *J. Org. Chem.*, 1980, 45, 1713–1715. tert-Butyl 1-piperazinecarboxylate (4.25 g, 23.0 mmol) and a catalytic quantity of sodium hydroxide (0.18 g) were added successively to a stirred solution of methyl 2-phenyl)propenoate (3.70 g, 23.0 mmol), in anhydrous THF (50 ml). The mixture was stirred at +25° C. for 16 h and then at 50–60° C. for 6 h before partitioning between ethyl acetate and water. The organic layer was separated and washed with water (×2) and brine (×2), and dried ($MgSO_4$). The solvent was removed under vacuum and the residue chromatographed on silica gel eluting with ethyl acetate/hexane (30:70) to give the title-piperazine (5.10 g, 65%), (250 MHz, $CDCl_3$) 1.45 (9H, s, $(Me)_3$), 2.33–2.58 (5H, m, 2 of $CH_2$ and CH of $CH_2$), 3.19 (1H, dd, J=12.6 and 10.4 Hz, CH of $CH_2$), 3.38 (4H, br s, 2 of $CH_2$), 3.68 (3H, s, $CO_2Me$), 3.84 (1H, dd, J=10.4 and 4.9 Hz, CH), 7.22–7.33 (5H, m, Ar-H).

b) (±)-1-tert-Butyloxycarbonyl-4-(3-hydroxy-2-phenylpropyl)piperazine

To a stirred solution of the preceding ester (2.5 g, 7.20 mmol), in anhydrous THF (100 ml), cooled to −60° C., was added diisobutylaluminium hydride (18 ml of a 1.0M solution in THF, 18.0 mmol) and the mixture stirred for 0.5 h before warming to +25°. After 4 h the reaction mixture was quenched by successive addition of methanol (3 ml), water (15 ml) and 4N NaOH solution (10 ml). The precipitated aluminium salts were removed by filtration and washed with $CH_2Cl_2$. The organic layer was separated, dried ($MgSO_4$), and the solvent removed in vacuo. The residue was chromatographed on silica gel eluting with ethyl acetate/hexane (1:1) to give the title-alcohol (0.55 g, 26%), δ(250 MHz, $CDCl_3$) 1.46 (9H, s, $(Me)_3$), 2.36–2.46 (2H, m, $CH_2$), 2.66–2.79 (3H, m, CH and $CH_2$), 2.97–3.04 (1H, m, CH of $CH_2$), 3.23–3.29 (1H, m, CH of $CH_2$), 3.42–3.56 (4H, m, 2 of $CH_2$), 3.82–3.87 (1H, m, CH of $CH_2$), 3.95–4.01 (1H, m, CH of $CH_2$), 7.15–7.33 (5H. m, Ar-H).

3. (±)-1-H-4-(3-Hydroxy-2- phenylpropyl) piperazine

A solution of the preceding N-Boc piperazine (0.55 g, 1.72 mmol) in 90% formic acid (15 ml) was stirred at room temperature for 16 h. The solvent was evaporated in vacuo and the residue neutralised by addition of aqueous $K_2CO_3$ (5 ml). The mixture was partitioned between water (15 ml) and n-butanol (50 ml×2). The organics were combined, the solvent removed under vacuum, and the residue chromatographed on silica gel eluting with $CH_2Cl_2/MeOH/NH_3$ (20:8:1) to give the desired NH-piperazine (0.11 g, 30%).

4. (±)-1-[3-(5-(1,2,4-Triazol-4-yl)-1H-indol-3-yl) propyl]-4-(3-hydroxy-2-phenylpropyl)piperazine 1.6 Hydrogen Oxalate 0.4 Diethyl etherate To a solution of Intermediate 1 (0.20 g, 0.83 mmol) in anhydrous THF (100 ml), at 0° C., was added triethylamine (0.167 g, 1.65 mmol) and methane sulphonyl chloride (0.19 g, 1.65 mmol) and the mixture warmed to room temperature and stirred for 1.5 h. The solvent was removed in vacuo and the residue partitioned between ethyl acetate (50 ml) and $K_2CO_3$ solution (10 ml). The aqueous was separated and extracted further with ethyl acetate (1×50 ml). The combined extracts were dried ($MgSO_4$) and evaporated and used in the next step without further purification. To a solution of the preceding mesylate (0.264 g, 0.825 mmol), in isopropyl alcohol (25 ml), was added powdered $K_2CO_3$ (0.114 g, 0.825 mmol), sodium iodide (82 mg, 0.55 mmol) and (±)-1-H-4-(3-hydroxy-2-phenylpropyl)-piperazine (0.11 g, 0.55 mmol), and the mixture stirred at 120° C. for 16 h. The mixture was cooled to room temperature and the solvent removed in vacuo. The residue was partitioned between aq. $K_2CO_3$ solution (5 ml) and ethyl acetate (×3). The combined extracts were dried ($MgSO_4$) and evaporated, and the residue chromatographed through silica gel eluting with $CH_2Cl_2/MeOH/NH_3$ (90:8:1) to give the title-indole (0.104 g, 43%). The 1.6 hydrogen oxalate salt was prepared. mp 137–140° C., (Found: C, 59.62: H, 6.67; N, 13.36. $C_{26}H_{32}N_6O$. 1.6 ($C_2H_2O_4$). 0.4 ($C_4H_{10}O$) requires C, 59.83; H, 6.39; N, 13.59%), m/e 445 $(M+1)^+$, δ(360 MHz, $D_6$-DMSO) 1.92–2.06 (2H, m, $CH_2$), 2.56–3.62 (17H, m, 8 of $CH_2$ and CH), 7.18–7.34 (7H, m, Ar-H), 7.50 (1H, d, J=8.6 Hz, Ar-H), 7.79 (1H, s, Ar-H), 9.01 (2H, s, Ar-H), 11.17 (1H, s, NH).

EXAMPLE 2

(±)-1-[3-(5-(1,2,4-Triazol-4-yl)-1H-indol-3-yl) propyl]-4-(3-methoxy-2-phenyloropyl)piperazine. Sesquioxalate 0.6 Hydrate 0.2 Diethyl etherate a) (±)-1-tert-Butoxycarbonyl-4-(3-methoxy-2-phenylpropyl)piperazine To a solution of Intermediate 2 (0.60 g, 1.88 mmol) in anhydrous DMF (20 ml), at 0° C., was added sodium hydride (0.113 g of a 60% dispersion in oil, 2.81 mmol) and the mixture stirred for 0.2 h, before adding methyl iodide (0.399 g, 2.81 mmol), dropwise. The mixture was warmed to room temperature, stirred for 2 h, and then partitioned between water and ethyl acetate. The organic phase was separated and washed with water (×2) and brine (×1). After drying ($MgSO_4$), the solvent was removed in vacuo and the crude product chromatographed through silica gel eluting with ethyl acetate/hexane (1:1) to give the desired methyl ether (0.365 g, 60%), δ(250 MHz, $CDCl_3$) 1.44 (9H, s, $(Me)_3$), 2.26–2.78 (6H, m, 3 of $CH_2$), 3.02–3.16 (1H, m, CH), 3.31 (3H, s, OMe). 3.34–3.40 (4H, m, 2 of $CH_2$), 3.53–3.69 (2H, m, $CH_2$), 7.19–7.34 (5H, m, Ar-H).

b) (±)-1-H-4-(3-Methoxy-2-phenylpropyl)piperazine

Prepared from the preceding N-Boc piperazine using the procedure described for Example 1 step 3 (81% yield), δ(360 MHz, $CDCl_3$) 2.30–2.52 (5H, m, 2 of $CH_2$ and CH of $CH_2$), 2.67 (1H, dd, J=12.7 and 7.8 Hz, CH of $CH_2$), 2.81–2.84 (4H, m, 2 of $CH_2$), 3.07–3.15 (1H, m, CH), 3.30 (3H, s, OMe), 3.56 (1H, dd, J=9.3 and 7.3 Hz, CH of $CH_2$), 3.67 (1H, dd, J=9.3 and 5.7 Hz, CH of $CH_2$), 7.18–7.32 (5H, m, Ar-H).

c) (±)-1-[3-(5-(1,2,4-Triazol-4-yl)-1H-indol-3-yl)propyl]-4-(3-methoxy-2-phenylpropyl)piperazine. Sesquioxalate 0.6 Hydrate 0.2 Diethyl etherate The title-compound was prepared from the mesylate of Intermediate 1 and 1H-4-(3-methoxy-2-phenylpropyl) piperazine using the coupling procedure described for Example 1 step 4. The sesquioxalate salt was prepared, mp 134–136° C., (Found: C, 59.56; H, 6.56; N, 13.85. $C_{27}H_{34}N_6O$. 1.5 ($C_2H_2O_4$). 0.6$H_2O$. 0.2 ($C_4H_{10}O$) requires C, 59.74, H, 6.54; N, 13.57%), m/e 459 (M+1)$^+$, δ(360 MHz, $D_6$-DMSO) 1.92–2.05 (2H, m, $CH_2$), 2.50–3.16 (15H, m, 7 of $CH_2$ and CH), 3.19 (3H, s, OMe), 3.45–3.57 (2H, m, $CH_2$), 7.17–7.34 (7H, m, Ar-H), 7.50 (1H, d, J=8.7 Hz, Ar-H), 7.79 (1H, d, J=2.0 Hz, Ar-H), 9.02 (2H, s, Ar-H), 11.17 (1H, s, NH).

EXAMPLE 3

(±)-1-[3-(5-(1,2,4-Triazol-4-yl)-1-H-indol-3-yl) propyl]-4-[2-(4-fluorophenyl-3-hydroxypropyl] piperazine. 1.3 Hydrogen Oxalate. 0.5 Diethyl etherate 1. Intermediate 3: 1-[3-(5-(1,2,4-Triazol-4-yl)-1H-indol-3-yl)propyl]-4-(H)-piperazine a) 5-Bromopentanal dimethyl acetal To a solution of 5-bromovaleryl chloride (50 g, 0.251 mol) in anhydrous THF (500 ml), at −78° C., was added lithium tri-tert-butoxyaluminohydride (1.0M solution in tetrahydrofuran, 300 ml: 0.30 mol), keeping the temperature below −70° C. The solution was stirred at −78° C. for 5 h and then quenched by dropwise addition of 2M hydrochloric acid (350 ml). The mixture was warmed to room temperature and stirred for 16 h. Diethyl ether (500 ml) was added, the aqueous phase separated and extracted further with ether (×2). The combined extracts were washed with saturated $Na_2CO_3$ solution (×1), water (×1) and brine (×2), dried ($Na_2SO_4$) and evaporated to give 5-bromovaleraldehyde (37.5 g, 91%). A solution of 5-bromovaleraldehyde (37.5 g, 0.227 mol) in methanol (250 ml) and concentrated sulphuric acid (0.5 ml) was stirred at room temperature for 3 h. The solvent was removed under vacuum and to the residue was added $K_2CO_3$ solution (50 ml) and diethyl ether (500 ml). The aqueous layer was separated and re-extracted with ether (×2). The combined extracts were washed with water and brine, dried ($Na_2SO_4$) and evaporated. The crude product was chromatographed on silica gel eluting with diethyl ether/hexane (1:9) to give the title-acetal (27.5 g, 57%). δ(250 MHz, $CDCl_3$) 1.43–1.67 (4H, m, 2 of $CH_2$); 1.83–1.94 (2H, m, $CH_2$); 3.38 (6H, s, CH(OMe)$_2$); 3.42 (2H, t, J=7 Hz, $CH_2$Br), 4.37 (1H, t, J=7 Hz, C$\underline{H}$(OMe)$_2$).

b) 5-[4-(tert-Butyloxycarbonyl)piperazin-1-yl]pentanal dimethyl acetal

A mixture of 5-bromovaleraldehyde dimethyl acetal (27.5 g, 0.13 mol), $Na_2CO_3$ (20.7 g, 0.195 mol), sodium iodide (19.5 g, 0.13 mol) and tert-butyl 1-piperazinecarboxylate (25.5 g, 0.137 mol), in dimethoxyethane (250 ml), was heated at 100° C. for 3 h. Aluminium foil was wrapped around the vessel to exclude light. The mixture was cooled to room temperature and filtered. The filtrate was evaporated under reduced pressure and then EtOAc (50 ml) added and the mixture filtered again to remove inorganic salts. The solvent was removed under vacuum and the residue chromatographed on silica gel eluting with EtOAc to give the title-product (25.7 g, 63%). δ(250 MHz, $CDCl_3$) 1.29–1.71 (6H, m, 3 of $CH_2$); 1.46 (9H, s, OC(Me)$_3$); 2.31–2.39 (6H, m, 3 of $CH_2$); 3.32 (6H, s, CH(OMe)$_2$); 3.41–3.45 (4H, m, 2 of $CH_2$); 4.36 (1H, t, J=6 Hz, C$\underline{H}$(OMe)$_2$).

c) 1-[3-(5-(1,2,4-Triazol-4-yl)-1H-indol-3-yl)propyl]-4-(H)-piperazine

A mixture of 4-(1,2,4-triazol-4-yl)phenylhydrazine (5.0 g, 28.6 mmol) and 5-[4-(tert-butyloxycarbonyl)piperazin-1-yl] pentanal dimethyl acetal (9.03 g, 28.6 mmol) in 4% sulphuric acid (150 ml) was heated at reflux for 48 h. The solution was cooled in an ice-bath, basified with solid $K_2CO_3$ and extracted with butan-1-ol (×3). The solvent was removed under vacuum and azeotroped with hexane (×2). The crude product was purified by chromatography on silica gel eluting with $CH_2Cl_2$/MeOH/$NH_3$ (30:8:1) to give the title-indole (3.9 g, 44%). δ(360 MHz, oxalate salt in $D_2O$) 2.12–2.24 (2H, m, $CH_2$); 2.93 (2H, t, J=7 Hz, $CH_2$); 3.46–3.76 (8H, m, 4 of $CH_2$) 7.37 (1H, dd, J=1.9 and 8.7 Hz, Ar-H); 7.39 (1H, s, Ar-H); 7.66 (1H, d, J=8.7, Ar-H); 7.82 (1H, d, J=1.9 Hz, Ar-H); 9.13 (2H, s, Triazole-H).

2. (±)-1-[3-(5-(1,2,4-Triazol-4-yl)-1H-indol-3-yl) propyl]-4-[2-(4-fluorophenyl)-2-(methoxycarbonyl) ethyl]piperazine Methyl 2-(4-fluorophenyl)propenoate was prepared using the procedures described by Howard, A. S. et al. in *J. Org. Chem.*, 1980, 45, 1713–1715. Intermediate 3 (0.308 g, 0.992 mmol) and sodium hydroxide (catalytic amount, 19 mg) were added successively to a stirred solution of methyl 2-(4-fluorophenyl)propenoate (0.179 g, 0.994 mmol), in methanol (5 ml). The mixture was stirred at 60° C. for 4.5 h and the solvent then removed in vacuo. The residue was partitioned between ethyl acetate and water, and the organic layer separated and washed with water and brine. After drying ($MgSO_4$), the solvent was removed in vacuo and the crude product was chromatographed through silica gel eluting with $CH_2Cl_2$/MeOH (9:1) to give the title-product (0.244 g, 50%), δ(250 MHz, $CDCl_3$) 1.82–2.01 (2H, m, $CH_2$), 2.34–2.81 (13H, m, 6 of $CH_2$ and CH of $CH_2$), 3.14 (1H, dd, J=12.6 and 10.2 Hz, CH of $CH_2$), 3.67 (3H, s, $CO_2Me$), 3.81 (1H, dd, J=10.2 and 5.1 Hz, CH), 6.96–7.31 (6H, m, Ar-H), 7.48 (1H, d, J=8.5 Hz, Ar-H), 7.56 (1H, d, J=2.0 Hz, Ar-H), 8.47 (2H, s, Ar-H), 8.50 (1H, br s, NH).

3. (±)-1-[3-(5-(1,2,4-Triazol-4-yl)-1H-indol-3-yl) propyl]-4-[2-(4-fluorophenyl)-3-hydroxypropyl] piperazine. 1.3 Hydrogen Oxalate 0.5 Diethyl etherate Lithium aluminium hydride (0.39 ml of a 1.0M solution in THF, 0.39 mmol) was added dropwise to a stirred solution of the preceding methyl ester (0.192 g, 0.391 mmol), in anhydrous THF (10 ml), at −17° C. The mixture was stirred at −20° C. for 2 h and a further portion of LiAlH$_4$ (0.2 ml of a 1.0M solution in THF, 0.2 mmol) then added. After 1 h the reaction mixture was quenched by addition of saturated Na$_2$SO$_4$ solution (0.6 ml) and the resulting precipitate was removed by filtration through celite. The solvent was removed in vacuo and the residue chromatographed through silica gel eluting with CH$_2$Cl$_2$/MeOH/NH$_3$ (60:8:1) to give the title-alcohol (0.152 g, 84%). The 1.3 hydrogen oxalate salt was prepared, mp 138–140° C. (Found: C, 59.39; H, 6.56; N, 13.40. C$_{26}$H$_{31}$N$_6$FO. 1.3 (C$_2$H$_2$O$_4$). 0.5 (C$_4$H$_{10}$O) requires C, 59.60; H, 6.31; N, 13.63%), m/e 463 (M+1)$^+$, δ(360 MHz, D$_6$-DMSO) 1.92–2.04 (2H, m, CH$_2$), 2.52–3.08 (15H, m, 7 of CH$_2$ and CH), 3.49–3.60 (2H, m, CH$_2$), 7.06–7.11 (2H, m, Ar-H), 7.26–7.33 (4H, m, Ar-H), 7.49 (1H, d, J=8.7 Hz, Ar-H), 7.78 (1H, d, J=2.0 Hz, Ar-H), 9.00 (2H, s, Ar-H), 11.16 (1H, s, NH).

EXAMPLE 4

(±)-1-[3-(5-(1,2,4-Triazol-4-yl)-1H-indol-3-yl)propyl]-4-[1-(4-fluorophenyl)prop-2-yl]-piperazine. 3.0 Hydrogen Oxalate. 1.5 Hydrate To a solution of Intermediate 3 (0.310 g. 1.0 mmol), in MeOH (30 ml), was added 4-fluorophenyl acetone (0.197 g, 1.3 mmol), glacial acetic acid (0.28 ml, 5.0 mmol) and sodium cyanoborohydride (0.158 g, 2.5 mmol), and the mixture stirred at room temperature for 16 h. Further portions of sodium cyanoborohydride (0.316 g, 5.0 mmol) and glacial acetic acid (0.56 ml, 10 mmol) were added and the mixture stirred for 2 h. The solvent was removed in vacuo and the residue partitioned between ethyl acetate (×3) and saturated K$_2$CO$_3$ solution. The organic layer was dried (Na$_2$SO$_4$) and evaporated under vacuum, and the residue chromatographed through silica gel eluting with CH$_2$Cl$_2$/MeOH (9:1) to give the title-phenethylpiperazine (0.065 g, 15%). The 3.0 hydrogen oxalate salt was prepared, mp 170–173° C., (Found: C, 51.53; H, 5.53; N, 11.38. C$_{26}$H$_{31}$N$_6$F. 3.0 (C$_2$H$_2$O$_4$). 1.5 H$_2$O requires C, 51.68; H, 5.42; N, 11.30%), m/e 447 (M+1)$^{+yl}$, δ(360 MHz on free base, CDCl$_3$) 1.01 (3H, d, J=4.5 Hz, Me), 2.02–2.12 (2H, m, CH$_2$), 2.42–2.48 (1H, m, CH of CH$_2$), 2.70–3.06 (13H, m, 6 of CH$_2$ and CH of CH$_2$), 3.38–4.00 (1H, m, CH), 6.95–6.99 (2H, m, Ar—H), 7.10–7.15 (3H, m, Ar—H), 7.24 (1H, s, Ar—H), 7.49 (1H, d, J=8.5 Hz, Ar—H), 7.57 (1H, d, J=2.0 Hz, Ar—H), 8.52 (2H, s, Ar—H).

EXAMPLE 5

(±)-1-[3-(5-(1,2,4-Triazol-4-yl)-1H-indol-3-yl)propyl]-4-[2-(4-fluorolohenyl)propyl]piperazine. 3.0 Hydrogen Oxalate. Monohydrate a) (±)-2-(4-Fluorophenyl)propyl bromide Lithium aluminium hydride (29.8 ml of a 1.0M solution in THF, 29.8 mmol) was added dropwise to a stirred solution of 4-fluoro-α-methylphenyl acetic acid (5.0 g, 29.8 mmol), in diethyl ether (100 ml), which had been cooled to −10° C. The mixture was warmed to +25° C. and stirred for 1 h before quenching with methanol (20 ml) and 4M NaOH (20 ml). The mixture was filtered and the solvent evaporated in vacuo. The residue was chromatographed on silica gel eluting with dichloromethane to give 2-(4-fluorophenyl)propyl alcohol (3.65 g, 79%). To a solution of the preceding alcohol (3.65 g, 23.7 mmol) and carbon tetrabromide (9.82, 29.62 mmol), in dichloromethane (75 ml), was added triphenylphosphine (9.31 g, 35.5 mmol), portionwise. The mixture was stirred for 1 h at room temperature and diethyl ether (50 ml) then added. The precipitated triphenylphosphine oxide was filtered off and the solvents removed in vacuo. The residue was chromatographed through silica gel eluting with ethyl acetate/hexane (1:2) to afford the desired bromide (3.05 g, 60%), δ(250 MHz, CDCl$_3$) 1.40 (3H, d, J=6.8 Hz, Me), 3.06–3.20 (1H, m, CH), 3.42–3.61 (2H, m, CH$_2$), 6.97–7.26 (4H, m, Ar—H).

b) (±)-1-[3-(5-(1,2,4-Triazol-4-yl)-1H-indol-3-yl)propyl]-4-[2-(4-fluorophenyl)propyl]piperazine. 3.0 Hydrogen Oxalate. Monohydrate A mixture of Intermediate 3 (0.31 g, 1.0 mmol), 2-(4-fluorophenyl)propyl bromide (0.228 g, 1.05 mmol), triethylamine (0.202 g, 2.0 mmol) and sodium iodide (0.165 g, 1.1 mmol), in DMF (20 ml) was heated at 90° C., with stirring, for 16 h. The mixture was cooled to room temperature and partitioned between dichloromethane and water. The CH$_2$Cl$_2$ layer was separated, dried (Na$_2$SO$_4$) and evaporated under vacuum. The crude product was chromatographed through silica gel eluting with CH$_2$Cl$_2$/MeOH/NH$_3$ (90:10:1) to give the title-indole (0.125 g, 28%). The 3.0 hydrogen oxalate monohydrate salt was prepared, mp 203–205° C., (Found: C, 52.11; H, 5.60; N, 11.45. C$_{26}$H$_{31}$N$_6$F. 3.0 (C$_2$H$_2$O$_4$) 1.0H$_2$O requires C, 52.31; H, 5.35; N, 11.44%), δ(360 MHz, D$_6$-DMSO) 1.17 (3H, d, J=6.8 Hz, Me), 1.92–2.06 (2H, m, CH$_2$), 2.44–3.26 (15H, m, 7 of CH$_2$ and CH), 7.08–7.13 (2H, m, Ar—H), 7.26–7.33 (4H, m, Ar—H), 7.50 (1H, d, J=8.6 Hz, Ar—H), 7.78 (1H, d, J=1.5 Hz, Ar—H), 9.01 (2H, s, Ar—H), 11.16 (1H, s, NH).

EXAMPLE 6

(±)-1-[3-(5-(1,2,4-Triazol-4-yl)-1H-indol-3-yl)propyl]-4-[1-(4-fluorophenyl)-3-hydroxyprop-2-yl]piperazine. Sesquioxalate 1.1 Hydrate a) (±)-2-Bromo-3-(4-fluorophenyl)propionic acid To a cooled (0° C., ice/salt bath) solution of DL-4-fluorophenylalanine (5.0 g, 27.0 mmol) and potassium bromide (10.65 g, 90.0 mmol) in 3M sulphuric acid (45 ml) was added sodium nitrite (2.64 g, 38.0 mmol) portionwise over a 0.5 h period. The mixture was stirred at 0° C. for 1 h and then at room temperature for 1 h. The mixture was diluted with water (50 ml) and extracted with ether (2×75 ml). The combined extracts were washed with water (2×75 ml), dried (MgSO$_4$) and evaporated in vacuo. The residue was chromatographed on silica gel eluting with CH$_2$Cl$_2$/MeOH/NH$_3$ (95:5:1) to give the title-acid (3.77 g, 56%), δ(250 MHz, CDCl$_3$) 3.22 (1H, dd, J=14.3 and 7.2 Hz, CH of CH$_2$), 3.43 (1H, dd, J=14.3 and 8.1 Hz, CH of CH$_2$), 4.38 (1H, dd, J=7.2 and 8.1 Hz, CH), 6.98–7.31 (4H, m, Ar—H).

b) (±)-Methyl 2-bromo-3-(4-fluorophenyl)propionate

To a solution of the preceding acid (2.0 g, 8.1 mmol), in anhydrous methanol (15 ml), at −5° C., was added thionyl chloride (1.6 g, 13.8 mmol), dropwise. The mixture was stirred at −5° C. for 0.1 h and then at room temperature for 0.5 h. The solvent was removed in vacuo and the resulting residue azeotroped with toluene (2×10 ml) before chromatographing through silica gel using CH$_2$Cl$_2$→CH$_2$Cl$_2$/MeOH (100→80:20) as eluant. The title-ester was isolated as a colourless oil (1.36 g, 64%), δ(250 MHz, CDCl$_3$) 3.22 (1H, dd, J=14.2 and 7.1 Hz, CH of CH$_2$), 3.43 (1H, dd, J=14.2 and 8.3 Hz, CH of CH$_2$), 3.74 (3H, s, CO$_2$Me), 4.36 (1H, dd, J=8.3 and 7.1 Hz, CH), 6.96–7.26 (4H, m, Ar—H).

c) (±)-1-[3-(5-(1,2,4-Triazol-4-yl)-1H-indol-3yl)propyl]-4-[1-(methoxycarbonyl)-2-(4-fluorophenyl)ethyl]piperazine To a stirred solution of the preceding bromide (0.287 g, 1.1 mmol), in anhydrous DMF (5 ml), was added Intermediate 3 (0.31 g, 1.0 mmol) and $K_2CO_3$ (0.152 g, 1.1 mmol). The mixture was heated at 50° C. for 0.75 h and a further portion of bromide (0.287 g, 1.1 mmol), as a solution in DMF (2 ml), was then added. The mixture was heated for a further 0.5 h and then cooled to room temperature and the solvent removed in vacuo. The resulting residue was partitioned between $CH_2Cl_2$ (2×25 ml) and water (50 ml) and the combined organics were dried ($Na_2SO_4$) and evaporated under vacuum. The residue was chromatographed through silica gel eluting with $CH_2Cl_2$/MeOH (90:10→80:20) to give the title-indole (0.224 g, 46%) as a yellow foam, δ(360 MHz, $CDCl_3$) 1.89–1.98 (2H, m, $CH_2$), 2.44–2.82 (12H, m, 6 of $CH_2$), 2.90 (1H, dd, J=13.5 and 6.0 Hz, CH of $CH_2$), 3.02 (1H, dd, J=13.5 and 9.4 Hz, CH of $CH_2$), 3.39 (1H, dd, J=9.4 and 6.0 Hz, CH), 3.59 (3H, s, $CO_2Me$), 6.92–6.97 (2H, m, Ar—H), 7.11–7.16 (4H, m, Ar—H), 7.48 (1H, d, J=8.4 Hz, Ar—H), 7.56 (1H, d, J=2.0 Hz, Ar—H), 8.43 (1H, br s, NH), 8.47 (2H, s, Ar—H), m/e 491 $(M+1)^+$.

d) (±)-1-[3-(5-(1,2,4-Triazol-4-yl)-1H-indol-3-yl)propyl]-4-[1-(4-fluorophenyl)-3-hydroxyprop-2-yl]piperazine Sesquioxalate. 1.1 Hydrate To a cooled (−10° C., dry ice/acetone bath) solution of the preceding indole (0.22 g, 0.4 6 mmol), in anhydrous THF (10 ml), was added $LiAlH_4$ (0.45 ml of a 1.0M solution in diethyl ether, 0.45 mmol) dropwise. After stirring at −10° C. for 1 h a further portion of $LiAlH_4$ (0.23 ml, 0.23 mmol) was added and the mixture stirred for 0.5 h. Saturated $Na_2SO_4$ solution (0.7 ml) was added dropwise and the mixture warmed to room temperature. The precipitate was removed by filtration, the solvent removed in vacuo, and the residue remaining was chromatographed through silica gel eluting with $CH_2Cl_2$/MeOH/$NH_3$ (90:10:0→80:20:0→80:20:1) to give the title-alcohol (0.137 g, 66%). The sesquioxalate monohydrate salt was prepared. mp 104° C. (dec.), (Found: C, 56.31; H, 6.15; N, 13.75. $C_{26}H_{31}N_6OF$. 1.5 ($C_2H_2O_4$). 1.1 $H_2O$ requires C, 56.41; H, 5.91; N, 13.61%), m/e 463 $(M+1)^+$, δ(360 MHz, $D_6$-DMSO) 1.92–2.06 (2H, m, $CH_2$), 2.56–3.12 (15H, m, 7 of $CH_2$ and CH), 3.36–3.47 (2H, m, $CH_2$), 7.07–7.12 (2H, m, Ar—H). 7.25–7.34 (4H, m, Ar—H), 7.51 (1H, d, J=8.6 Hz, Ar—H), 7.80 (1H, d, J=1.5 Hz, Ar—H), 9.02 (2H, s, Ar—H), 11.17 (1H, s, NH).

EXAMPLE 7

(±)-1-[3-(5-(1,2,4-Triazol-4-yl)-1H-indol-3-yl)propyl]-4-[1-(4-fluorophenyl)3-methoxyprop-2-yl]piperazine. Sesquioxalate Hemihydrate To a solution of Example 6 (0.115 g, 0.25 mmol) in anhydrous THF (10 ml), at 0° C. (ice/water bath), was added triethylamine (0.05 g, 0.50 mmol) and methane sulphonyl chloride (0.057 g, 0.50 mmol) and the mixture stirred at 0° C. for 0.3 h and at room temperature for 0.3 h. The mixture was added portionwise to a solution of sodium (0.115 g, 5.0 mmol) in methanol (10 ml) and heated in a sealed tube at 75° C. for 0.5 h. The solvent was then removed in vacuo and the residue partitioned between ethyl acetate (2×50 ml) and water (50 ml). The organics were combined, dried ($Na_2SO_4$) and evaporated in uacuo. The crude product was chromatographed through silica gel eluting with $CH_2Cl_2$/MeOH/$NH_3$ (95:5:1→90:10:1) to give the title-methyl ether (62 mg, 52%). The sesquioxalate hemihydrate salt was prepared, mp 88° C. (dec.), (Found: C, 57.96; H, 6.06; N, 13.36. $C_{27}H_{33}N_6FO$. 1.5 ($C_2H_2O_4$). 0.5 ($H_2O$) requires C, 58.06: H, 6.01; N, 13.54%), m/e 477 $(M+1)^+$, δ(360 MHz, $D_6$-DMSO) 1.94–2.08 (2H, m, $CH_2$), 2.30–3.12 (15H, m, 7 of $CH_2$ and CH), 3.20 (3H, s, OMe), 3.28–3.38 (2H, s, $CH_2$), 7.06–7.11 (2H, m, Ar—H), 7.23–7.34 (4H, m, Ar—H), 7.51 (1H, d, J=8.4 Hz, Ar—H), 7.80 (1H, d, J=1.5 Hz, Ar—H), 9.02 (2H, s, Ar—H), 11.18 (1H, s, NH).

EXAMPLE 8

(±)-1-[3-(5-(Imidazol-1-yl)-1H-indol-3-yl)propyl]-4-[2-(phenyl)propyl]piperazine. 3.0 Hydrogen Maleate. 0.1 Hydrate 1. 1-[3-(5-(Imidazol-1-yl)-1H-indol-3-yl)propyl]-4-(H)-piperazine a) 4-(Imidazol-1-yl)nitrobenzene To a stirred solution of imidazole (34.1 g, 0.50 mol) in DMF (300 ml) under Ar, was added portionwise, over 23 minutes, 60% NaH in oil (20.02 g, 0.50 mol). The mixture was then stirred at room temperature for 18 minutes before adding dropwise, over 40 minutes, a solution of 1-fluoro-4-nitrobenzene (70.62 g, 0.50 mol) in DMF (60 ml). The mixture was then stirred at room temperature overnight. Water (600 ml) was then added and the solid was filtered off, washed with water, then stirred in boiling ethyl acetate (400 ml), allowed to cool and filtered, washing the solid with more ethyl acetate (50 ml), then petroleum ether (250 ml). The filtrate, now containing more solid, was refiltered and washed with petroleum ether. The combined solids were dried in a vacuum desiccator overnight to give 90.14 g (95%) of the title compound as a yellow solid. $δ_H$ (360 MHz, DMSO-$d_6$) 7.19 (1H, t, J=1.1 Hz), 7.97–8.03 (3H, m), 8.38 (2H, d, J=9.2 Hz), 8.52 (1H, t).

b) 4-(Imidazol-1-yl)aniline. Dihydrochloride

A mixture of 4-(imidazol-1-yl)nitrobenzene (89.60 g, 0.474 mol) and 10% palladium on carbon (4.50 g) in ethanol (1200 ml) and 5N HCl (189 ml) was hydrogenated in two batches at 40 psi for 80 minutes. Water (450 ml) was then added to dissolve the product and the catalyst was removed by filtration. washing with more water, and the combined filtrates were evaporated in vacuo, using finally a freeze drier, to give 105.4 g (96%) of the title compound as a cream solid. $δ_H$ (250 MHz, $D_2O$) 7.22 (2H, d, J=8.8 Hz), 7.35 (1H, t, J=2.1 Hz), 7.44 (2H, d, J=9.0 Hz). 7.59 (1H, t, J=1.8 Hz), 8.89 (1H, t, J=1.5 Hz).

c) 4-(Imidazol-1-yl)phenylhydrazine. Dihydrochloride

To a cooled (−15° C.) and stirred suspension of 4-(imidazol-1-yl)aniline dihydrochloride (20 g, 86.16 mmol) in concentrated hydrochloric acid (100 ml) was added dropwise, over 1 hour, a solution of sodium nitrite (6.25 g, 9.05 mmol) in water (40 ml). After a further 10 minutes of stirring at −12° C., the mixture was quickly filtered to remove a solid, and the filtrate was added portionwise to a cooled (−20° C.) and stirred solution of tin (II) chloride dihydrate (100 g) in concentrated hydrochloric acid (50 ml) at such a rate as to maintain the internal temperature below −10° C. (15 minutes). The mixture was allowed to warm to 5° C. over 30 minutes, and the solid was collected and washed with diethyl ether (4×100 ml). The above solid was suspended in water (200 ml) and basified with 4N sodium hydroxide solution and extracted with ethyl acetate (5×500 ml). The combined organic solutions were dried ($Na_2SO_4$) and filtered. The filtrate was vigorously stirred while hydrogen chloride was being bubbled through the solution until a deep red mixture was obtained. Stirring was continued for a further 20 minutes to give a cream solid which was collected by filtration and dried over phosphorus pentoxide-potassium hydroxide under high vacuum to leave 12.7 g (60%) of the title compound: $δ_H$ (360 MHz, DMSO-$d_6$) 7.20 (2H, d, J=9.0 Hz), 7.73 (2H, d, J=9.0 Hz), 7.91 (1H, t, J=1.5 Hz), 8.23 (1H, t, J=1.7 Hz), 9.71 (1H, t, J=1.3 Hz).

d) 1-[3-(5-(Imidazol-1-yl)-1H-indol-3-yl)propyl]-4-(H)-piperazine

Prepared from 4-(imidazol-1-yl)phenylhydrazine and 5-[4-(tert-butyloxcarbonyl)piperazin-1-yl]pentanal dimethyl acetal using the procedure described for Example 3, Intermediate 3, δ(250 MHz, $D_6$-DMSO) 1.86–1.97 (2H, m, $CH_2$), 2.37–3.66 (12H, m, 6 of $CH_2$), 4.23 (1H, br s, NH), 7.20 (1H, s, Ar—H), 7.35–7.40 (2H, m, Ar—H), 7.56 (1H, d, J=8.6 Hz, Ar—H), 7.77 (1H, d, J=2.0 Hz, Ar—H), 7.80 (1H, d, J=2.0 Hz, Ar—H), 8.24 (1H, s, Ar—H), 11.11 (1H, s, NH).

2. (±)-1-[3-(5-(Imidazol-1-yl)-1H-indol-3-yl)propyl]-4-[2-phenyl)propyl]piperazine. 3.0 Hydrogen Maleate. 0.1 Hydrate Sodium cyanoborohydride (78 mg, 1.25 mmol) was added to a solution of 1-[3-(5-(imidazol-1-yl)-1H-indol-3-yl)propyl]-4-(H)-piperazine (0.308 g, 1.0 mmol) and glacial acetic acid (0.15 g, 2.5 mmol), in methanol (40 ml) at −10° C. A solution of (±)-2-phenylpropionaldehyde (0.16 g, 1.12 mmol), in methanol (10 ml), was added dropwise and the reaction mixture was warmed to room temperature and stirred for 16 h. The solution was basified by addition of saturated $K_2CO_3$ solution and the methanol was evaporated in vacuo. The resulting aqueous was extracted with $CH_2Cl_2$ (3×100 ml) and the combined extracts were dried ($Na_2SO_4$) and evaporated, and the residue chromatographed on silica gel eluting with 10% methanol/$CH_2Cl_2$ to give the title-product (0.263 g, 62%). The 3.0 hydrogen maleate 0.1 hydrate salt was prepared, mp 140–141° C., (Found: C, 59.19; H, 5.96; N, 9.26. $C_{27}H_{33}N_5$ 3.0 ($C_4H_4O_4$). 0.1 $H_2O$ requires C, 60.23; H, 5.86; N, 9.01%), m/e 428 (M+1)$^+$, δ(360 MHz, $D_6$-DMSO) 1.19 (3H, d, J=6.9 Hz, Me), 1.94–2.06 (2H, m, $CH_2$), 2.52–3.60 (15H, m, CH and 7 of $CH_2$), 6.13 (maleate-H's), 7.17–7.39 (7H, m, Ar—H), 7.53 (1H, d, J=8.6 Hz, Ar—H), 7.55 (1H, s, Ar—H), 7.83 (1H, d, J=2.0 Hz, Ar—H), 7.97 (1H, s, NH). 8.93 (1H, s, Ar—H), 11.19 (1H, s, NH).

EXAMPLE 9

(±)-1-[3-(5-(Imidazol-1-yl)-1H-indol-3-yl)propyl]-4-[2-(4-fluorophenyl)-propyl]-piperazine. 2.5 Hydrogen Maleate. 0.75 Hydrate The title compound was prepared by alkylation of 1-[3-(5-imidazol-1-yl)-1H-indol-3-yl)propyl]-4-(H)-piperazine with (±)-2-(4-fluorophenyl)-propyl bromide as described for the synthesis of Example 5. The 2.5 hydrogen maleate 0.75 hydrate salt was prepared. mp 137–138° C. (Found: C, 59.29: H, 5.88; N, 9.29. $C_{27}H_{32}N_5F$. 2.5($C_4H_4O_4$). 0.75$H_2O$ requires C, 59.31; H, 5.85; N, 9.35%), m/e 446 (M+1)$^+$, δ(250 MHz, $CDCl_3$, free base) 1.23 (3H, d, J=6.9 Hz, Me), 1.85–1.97 (2H, m, $CH_2$), 2.32–2.60 (12H, m, 6 of $CH_2$), 2.77 (2H, t, J=7.5 Hz, $CH_2$), 2.85–2.98 (1H, m, CH), 6.92–7.21 (7H, m, Ar—H), 7.29 (1H, s, Ar—H), 7.41 (1H, d, J=8.6 Hz, Ar—H), 7.56 (1H, d, J=2.0 Hz, Ar—H), 7.84 (1H, s, Ar—H), 8.58 (1H, s, NH).

EXAMPLE 10

(±)-1-[3-(5-(1,2,4-Triazol-1-ylmethyl)-1H-indol-3-yl)propyl]-4-[2-(4-fluorophenyl)propyl]piperazine. Dihydrogen Maleate 1. 3-[5-(1,2,4-Triazol-1-ylmethyl)-1H-indol-3-yl]propan-1-ol 3,4-Dihydro-2H-pyran (3.9 ml, 42.7 mmol) was added to a stirred solution of 4-(1,2,4-triazol-1-ylmethyl) phenylhydrazine (EP 497,512; 4.0 g, 21.1 mmol) in dioxane/water/5N HCl (38 ml/14 ml/4.7 ml) and stirred at room temperature for 1.75 h. The solution was then refluxed for 1.5 h and the solvent removed under vacuum. The residue was taken up into $CH_2Cl_2$ and saturated aqueous $K_2CO_3$ solution. The aqueous was separated and further extracted with $CH_2Cl_2$ (×4). The combined organic extracts were dried ($MgSO_4$) and evaporated and the residue chromatographed on silica gel eluting with $CH_2Cl_2$/MeOH/$NH_3$ (80:8:1) to give the title-indole (0.919 g, 17%), δ(250 MHz, $CDCl_3$) 1.91–2.03 (2H, m, $CH_2$), 2.84 (2H, t, J=7.9 Hz, $CH_2$), 3.73 (2H, t, J=7.9 Hz, $CH_2$), 5.43 (2H, s, $CH_2$), 7.04 (1H, d, J=2.3 Hz, Ar—H), 7.11 (1H, dd, J=2.3 and 8.3 Hz, Ar—H), 7.35 (1H, d, J=8.3 Hz, Ar—H), 7.58 (1H, s, Ar—H). 7.97 (1H, s, Ar—H). 8.02 (1H, s, Ar—H), 8.18 (1H, s, NH).

2. (±)-4-[2-(4-Fluorophenyl)propyl]piperazine

A mixture of (±)-2-(4-fluorophenyl)propyl bromide (3.03 g, 13.96 mmol), N-Boc-piperazine (2.60 g, 13.96 mmol), potassium carbonate (3.86 g, 27.93 mmol) and sodium iodide (2.09 g, 13.96 mmol), in anhydrous isopropyl alcohol (100 ml) was refluxed for 16 h. The inorganics were filtered off and the solvent evaporated in vacuo. The resulting residue was partitioned between $CH_2Cl_2$ (3×150 ml) and water (50 ml). The combined extracts were dried ($Na_2SO_4$) and evaporated and the residue chromatographed on silica gel eluting with hexane to give 1.8 g (40%) of product. This material was dissolved in 99% formic acid (50 ml) and the solution stirred at room temperature for 16 h. The solvent was removed under vacuum and the residue basified by addition of saturated $K_2CO_3$ solution and then extracted with n-butanol (100 ml). The n-butanol was evaporated in vacuo and the residue chromatographed on silica gel eluting with $CH_2Cl_2$/MeOH/$NH_3$ (60:8:1) to give the title-product (0.34 g, 27%), δ(360 MHz, $CDCl_3$) 1.24 (3H, d, J=7.0 Hz, Me), 2.30–2.46 (6H, m, 3 of $CH_2$), 2.78–2.98 (5H, m, 2 of $CH_2$ and CH), 6.94–7.00 (2H, m, Ar—H), 7.12–7.26 (2H, m, Ar—H).

3. (±)-1-[3-(5-(1,2,4-Triazol-1-ylmethyl)-1H-indol-3-yl)propyl]-4-[2-(4-fluorophenyl)propyl]piperazine. Dihydrogen Maleate The title-compound was prepared from (±)-4-[2-(4-fluorophenyl)propyl]piperazine and 3-[5-(1,2,4-triazol-1-ylmethyl)-1H-indol-3-yl]propan-1-ol using the procedure described for Example 1. The dihydrogen maleate salt was prepared, mp 171–172° C., (Found: C, 60.66; H, 5.95; N, 12.11. $C_{27}H_{33}N_6F$. 2.0 ($C_4H_4O_4$) requires C, 60.68; H, 5.97; N, 12.31%), m/e 461 (M+1)$^+$, δ(250 MHz, $CDCl_3$, free base) 1.24 (3H, d, J=6.9 Hz, Me), 1.83–1.95 (2H, m, $CH_2$), 2.39–2.56 (12H, m, 6 of $CH_2$), 2.74 (2H, t, J=7.7 Hz, $CH_2$), 2.85–3.00 (1H, m, CH), 5.42 (2H, s, $CH_2$), 6.93–7.18 (6H, m, Ar—H), 7.35 (1H, d, J=8.3 Hz, Ar—H), 7.57 (1H, s, Ar—H). 7.96 (1H, s, Ar—H), 7.98 (1H, s, Ar—H), 8.10 (1H, br s, NH).

EXAMPLE 11

(±)-1-[3-(5-(1,2,4-Triazol-4-yl)-1H-indol-3-yl)propyl]-4-[2-(3-fluorophenyl)-3-methoxypropyl]piperazine. 3.5 Hydrogen Oxalate. 1.5 Diethyl Etherate The title compound was prepared from 3-[5-(1,2,4-triazol-4-yl)-1H-indol-3-yl]propan-1-ol using the procedures described for Example 2. The 3.5 hydrogen oxalate 1.5 diethyl etherate salt was prepared, mp 145° C. (dec.), (Found: C, 53.21; H, 6.14; N, 9.31. $C_{27}H_{33}N_6OF$. 3.5 $(C_2H_2O_4)$. 1.5$(C_4H_{10}O)$ requires C, 53.20; H, 6.06; N, 9.58%), m/e 477 (M+1)$^+$, δ(360 MHz, CDCl$_3$, free base) 1.88–2.02 (2H, m, CH$_2$), 2.42–2.74 (12H, m, 6 of CH$_2$), 2.78 (2H, t, J=7.4 Hz, CH$_2$), 3.02–3.14 (1H, m, CH), 3.29 (3H, s, OMe), 3.49–3.64 (2H, s, CH$_2$OMe), 6.88–7.00 (3H, m, Ar—H), 7.13–7.27 (3H, m, Ar—H), 7.46 (1H, d, J=8.5 Hz, Ar—H), 7.55 (1H, d, J=2.0 Hz, Ar—H), 8.35 (1H, s, NH), 8.46 (2H, s, Ar—H).

EXAMPLE 12

(±)-1-[3-(5-(1,2,3-Triazol-1-yl)-1H-indol-3-yl) propyl]-4-[2-(4-fluorophenyl)propyl]piperazine. Dihydrogen Maleate

1. 1-[3-(5-(1,2,3-Triazol-1-yl)-1H-indol-3-yl) propyl]-4(H)-piperazine

The title compound was prepared from 4-(1,2,3-triazol-1-yl)phenyl hydrazine (EP 497,512) and 3,4-dihydro-2H-pyran using the procedures described for Example 1, Intermediate 1, δ(250 MHz, CDCl$_3$) 1.94–2.05 (2H, m, CH$_2$), 2.89 (2H, t, J=7.5 Hz, CH$_2$), 3.65 (1H, br s, OH), 3.74 (2H, t, J=7.5 Hz, CH$_2$), 7.14 (1H, d, J=2.3 Hz, Ar—H), 7.44–7.52 (2H, m, Ar—H), 7.85 (1H, s, Ar—H), 7.92 (1H, s, Ar—H), 8.00 (1H, s, Ar—H), 8.43 (1H, br s, NH).

2. (±)-1-[3-(5-(1,2,3-Triazol-1-yl)-1H-indol-3-yl) propyl]-4-[2-(4-fluorophenyl)propyl]piperazine. Dihydrogen Maleate The title-compound was prepared from the preceding homotryptophol and (±)-4-[2-(4-fluorophenyl)propyl] piperazine using the procedures described for Example 10. The dihydrogen maleate salt was prepared, mp 177–178° C., (Found: C, 60.19; H, 5.71; N, 12.21. $C_{26}H_{31}N_6F$. 2.0 $(C_4H_4O_4)$ requires C, 60.17; H, 5.79; N, 12.38%), m/e 447 (M+1)$^+$, δ(360 MHz, D$_6$-DMSO) 1.17 (3H, d, J=6.9 Hz, Me), 1.94–2.06 (2H, m, CH$_2$), 2.50–3.56 (15H, m, CH and 7 of CH$_2$), 6.14 (maleate-H's), 7.08–7.13 (2H, m, Ar—H), 7.26–7.30 (2H, m, Ar—H), 7.34 (1H, d, J=2.0 Hz, Ar—H). 7.52–7.57 (2H, m, Ar—H), 7.94 (1H, s, Ar—H), 8.00 (1H, s, Ar—H), 8.70 (1H, s, Ar—H), 11.18 (1H, s, NH).

EXAMPLE 13

1-[3-(5-(1,2,4-Triazol-4-yl)-1H-indol-3-yl)propyl]-4-[2-(3-fluorophenyl)-3,3,3-trifluoropropyl]piperazine. Sequioxalate. Hemihydrate

1. 3,3,3-Trifluoro-2-(3-fluorophenyl) propionaldehyde

The title-compound was prepared as described in EP 0240978, δ(250 MHz, CDCl$_3$) 4.22–4.33 (1H, m, CH), 7.04–7.48 (4H, m, Ar—H), 9.76–9.80 (1H, m, CHO).

2. 1-[3-(5-(1,2,4-Triazol-4-yl)-1H-indol-3-yl) propyl]-4-[2-(3-fluorophenyl)-3,3,3-trifluoropropyl] piperazine. Sequioxalate. Hemihydrate The title-compound was prepared as described for Example 8, step 2. The sesquioxalate hemihydrate salt was prepared. mp 105° C. (dec.), (Found: C, 53.73: H, 5.14; N, 13.16. $C_{26}H_{28}N_6F_4$. 1.5$(C_2H_2O_4)$. 0.5H$_2$O requires C, 54.04: H, 5.00; N, 13.04%), m/e 501 (M+1)$^+$, δ(360 MHz, D$_6$DMSO) 1.92–2.04 (2H, m, CH$_2$), 2.42–4.20 (15H, m, CH and 7 of CH$_2$), 7.14– 7.50 (7H, m, Ar—H), 7.77 (1H, s, Ar—H), 9.00 (2H, s, Ar—H), 11.15 (1H, s, NH).

EXAMPLE 14

1-[3-(5-(1,2,4-Triazol-4-yl)-1H-indol-3-yl)propyl]-4-(2,2-difluoro-2-phenylethyl)piperazine. Hydrogen Oxalate

1. 2,2-Difluoro-2-phenylacetic acid a) Ethyl benzoylformate (1.13 g, 0.0063 mol) was dissolved in anhydrous CH$_2$Cl$_2$ (30 ml) and diethylaminosulfurtrifluoride (DAST, 1.0 ml, 0.0086 mol) added. The reaction mixture was heated to 40° C. and left stirring for 4 h. The reaction was cooled, poured into a mixture of NaHCO$_3$/ice-water and the product extracted into ether (50 ml). The organic layer was dried over MgSO$_4$, evaporated and the residue chromatographed on silica eluting with 2% ether/petrol to yield 0.96 g (76%) of 2,2-difluoro-2-phenylacetic acid ethyl ester as a colourless oil. δ(250 MHz, CDCl$_3$) 1.26 (3H, t), 4.29 (2H, q), 7.50 (3H, m), 7.62 (2H, m).

b) The ethyl ester from above was dissolved in H$_2$O/THF (1:1, 20 ml) and cooled to 0° C. Sodium hydroxide (1 g) was added and the reaction stirred for 1 h. TLC (5% ether/hexane) showed complete disappearance of the starting ester. The reaction was acidified to pH 2 with 10% HCl and the product extracted into ether. The organic layer was dried over MgSO$_4$, filtered and evaporated in vacuo to yield the title compound as a solid (1.0 g).

2. 1-(tert-Butoxycarbonyl)-4-(2,2-difluoro-2-phenylacetamido)-piperazine 2,2-Difluoro-2-phenylacetic acid (0.600 g, 0.0035 mol). N-(tert-butoxycarbonyl)piperazine (0.714 g, 0.0038 mol) and triethylamine (0.53 ml, 0.0038 mol) were added sequentially to 20 ml anhydrous dichloromethane under N$_2$ at 25° C. Bis(2-oxo-3-oxazolidinyl)phosphinic chloride (0.967 g, 0.0038 mol) was added and the reaction stirred for 2 h. The reaction mixture was diluted with ethyl acetate (50 ml) and washed with H$_2$O (20 ml), brine, dried over MgSO$_4$ and evaporated. The residue was chromatographed on silica eluting with 20–40% ethyl acetate-hexane to yield the title compound as a colourless oil (1.0 g, 84%). δ(250 MHz, CDCl$_3$) 1.44 (9H, s), 3.21 (2H, m), 3.24 (4H, m), 3.44 (2H, m), 7.45–7.62 (5H, m).

3. N-(2,2-Difluoro-2-phenylethyl)piperazine 1-(tert-Butoxycarbonyl)-4-(2,2-difluoro-2-phenylacetamido)piperazine (1.0g, 0.0029 mol) was dissolved in anhydrous THF (10 ml) and borane-tetrahydrofuran complex (1.0M in THF, 4.4 ml, 0.0044 mol) added at 25° C., under N$_2$. The reaction mixture was heated to reflux for 4 h, cooled, and quenched with MeOH (2 ml). The volatile solvents were removed in vacuo and the residue dissolved in acetone (15 ml). The flask was cooled to 0° C. and treated with 15 ml of 4N HCl. The reaction was stirred at 25° C. for 30min and basified with 4N NaOH. The compound was extracted into EtOAc (3×50 ml), the organic layer dried over MgSO$_4$ and the solvent removed in vacuo. The residue was chromatographed on alumina (Grade III), eluting with 1–5% MeOH/CH$_2$Cl$_2$, then NH$_3$:MeOH:CH$_2$Cl$_2$ (1:5:95) to yield the amine as an oil (0.530 g). δ(250 MHz, CDCl$_3$) 2.52 (4H, m), 2.79 (4H, m), 2.93 (3H, t, J=5 Hz), 7.41 (3H, m), 7.49 (2H, m).

4. 1-[3-(5-(1,2,4-Triazol-4-yl)-1H-indol-3-yl) propyl]-4-(2,2-difluoro-2-phenylethyl)piperazine. Hydrogen Oxalate Prepared according to Example 1. The hydrogen oxalate salt was prepared, mp 175–177° C., m/e 451 (M+1)$^+$, δ(250

MHz, CDCl$_3$), 1.90 (4H, m), 2.43 (4H, m), 2.60 (4H, m), 2.77 (2H, t, J=3 Hz), 2.94 (2H, t, J=8 Hz), 7.12 (2H, m), 7.39–7.45 (5H, m), 7.51 (2H, m), 8.42 (1H, br s, NH), 8.46 (2H, s, Ar—H).

EXAMPLE 15

(±)-1-[3-(5-(1,2,4-Triazol-4-yl)-1H-indol-3-yl) propyl]-4-(2-phenylpropyl)piperazine. 2.1 Hydrogen Maleate. 0.5 Hydrate To a solution of Intermediate 3 (0.250 g, 0.8 mmol) in MeOH (35 ml) was added 2-phenylpropionaldehyde (0.134 g, 1.0 mmol), glacial acetic acid (0.119 ml, 2.15 mmol) and sodium cyanoborohydride (0.063 g, 1.0 mmol) and the mixture stirred at room temperature for 2 h. The solvent was removed in vacuo and the residue partitioned between dichloromethane (2×) and saturated K$_2$CO$_3$ solution. The organic layer was dried (MgSO$_4$) and evaporated under vacuum, and the residue chromatographed on silica gel eluting with CH$_2$Cl$_2$/MeOH/NH$_3$ (90:5:0.5) to give the title phenethyl piperazine (0.10 g, 29%). The 2.1 hydrogen maleate 0.5 hydrate salt was prepared, mp. 166–167° C., (Found: C, 60.94; H, 6.06; N, 12.04. C$_{26}$H$_{32}$N$_6$. 2.1 (C$_4$H$_4$O$_4$) 0.5 H$_2$O requires C, 60.64; H, 6.12; N, 12.33%), m/e 429 (M+1)$^+$, δ(250 MHz, on free base, CDCl$_3$) 1.24 (3H, d, J=6.90 Hz, CH$_3$), 1.90 (2H, m, CH$_2$), 2.39–2.47 (12H, m, 6 of CH$_2$), 2.74–2.80 (2H, m, CH$_2$), 2.86–3.00 (1H, m, CH), 6.98–7.31 (7H, m, Ar—H), 7.50 (1H, d, J=8.54 Hz, Ar—H), 7.55 (1H, d, J=2.03 Hz, Ar—H), 8.47 (2H, s, Ar—H), 9.30 (1H, s, NH).

EXAMPLE 16

(±)-1-[3-(5-(1,2,4-Triazol-4-yl)-1H-indol-3-yl) propyl]-4-[2-(3-fluorophenyl)-3-hydroxypropyl] piperazine. 2.625 Hydrogen Oxalate. 1.5 Diethyl etherate The title compound was prepared from methyl 2-(3-fluorophenyl)propenoate using the procedures described for Example 3, (Found: C, 55.32; H, 6.76; N, 9.99. C$_{26}$H$_{31}$N$_6$FO. 2.625(C$_2$H$_2$O$_4$). 1.5(C$_2$H$_5$)$_2$O requires C, 55.22; H, 6.37; N, 10.37%), m/e 463 (M+1)$^+$.

EXAMPLE 17

(±)-1-[3-(5-(2-Methylimidazol-1-yl)-1H-indol-3-yl) propyl]-4-[2-(4-fluorophenyl)propyl]piperazine. 3.25 Hydrogen Maleate The title-compound was prepared from 4-(2-methylimidazol-1-yl)phenylhydrazine using the procedures described for Example 8 part 1 and Example 5 part b, (Found: C, 58.65; H, 5.92; N, 8.71. C$_{28}$H$_{34}$N$_5$F. 3.25 (C$_4$H$_4$O$_4$) requires C, 58.85; H, 5.66; N, 8.37%).

We claim:

1. A compound of formula I, or a pharmaceutically acceptable salt thereof:

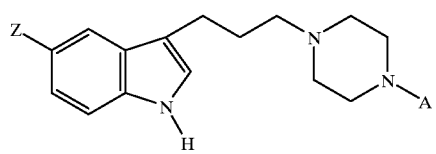

(I)

wherein

A represents a group of formula (i) or (ii):

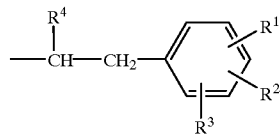

(i)

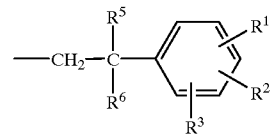

(ii)

in which

R$^1$ represents hydrogen, halogen, trifluoromethyl, C$_{1-6}$ alkoxy or a group of formula (a):

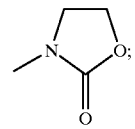

(a)

R$^2$ and R$^3$ independently represent hydrogen, halogen, trifluoromethyl or C$_{1-6}$ alkoxy;

R$^4$ represents C$_{1-6}$ alkyl, hydroxy(C$_{1-6}$)alkyl or C$_{1-6}$ alkoxy(C$_{1-6}$)alkyl;

R$^5$ represents halogen, trifluoromethyl, C$_{1-6}$ alkyl, hydroxy(C$_{1-6}$)alkyl or C$_{1-6}$ alkoxy(C$_{1-6}$)alkyl; and R$^6$ represents hydrogen or halogen;

Z represents a group of formula (Za), (Zb) or (Zc):

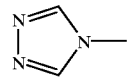

(Za)

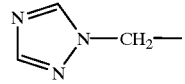

(Zb)

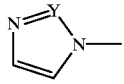

(Zc)

in which

Y represents nitrogen or C—R$^7$; and

R$^7$ represents hydrogen or C$_{1-6}$ alkyl.

2. A compound as claimed in claim 1 wherein A represents a group of formula (i) or (ii) in which R$^5$ represents C$_{1-6}$ alkyl, hydroxy(C$_{1-6}$)alkyl or C$_{1-6}$ alkoxy(C$_{1-6}$)alkyl, and R$^6$ represents hydrogen; and Z represents a group of formula (Za) as defined in claim 1.

3. A compound as claimed in claim 1 represented by formula II, and pharmaceutically acceptable salts thereof:

(II)

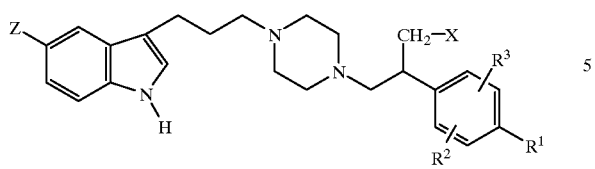

wherein Z, $R^1$, $R^2$ and $R^3$ are as defined in claim 1; and
X represents hydrogen, hydroxy or methoxy.

4. A compound selected from:
1-[3-(5-(1,2,4-triazol-4-yl)-1H-indol-3-yl)propyl]-4-(3-hydroxy-2-phenylpropyl)piperazine;
1-[3-(5-(1,2,4-triazol-4-yl)-1H-indol-3-yl)propyl]-4-(3-methoxy-2-phenylpropyl)piperazine;
1-[3-(5-(1,2,4-triazol-4-yl)-1H-indol-3-yl)propyl]-4-[2-(4-fluorophenyl)-3-hydroxypropyl]piperazine;
1-[3-(5-(1,2,4-triazol-4-yl)-1H-indol-3-yl)propyl]-4-[1-(4-fluor0phenyl)prop-2-yl]piperazine;
1-[3-(5-(1,2,4-triazol-4-yl)-1H-indol-3-yl)propyl]-4-[2-(4-fluorophenyl)propyl]piperazine;
1-[3-(5-(1,2,4-triazol-4-yl)-1H-indol-3-yl)propyl]-4-[1-(4-fluorophenyl)-3-hydroxyprop-2-yl]piperazine;
1-[3-(5-(1,2,4-triazol-4-yl)-1H-indol-3-yl)propyl]-4-[1-(4-fluorophenyl)-3-methoxyprop-2-yl]piperazine;
and pharmaceutically acceptable salts thereof.

5. A compound selected from:
1-[3-(5-(imidazol-1-yl)-1H-indol-3-yl)propyl]-4-(2-phenylpropyl)piperazine;
1-[3-(5-(imidazol-1-yl)-1H-indol-3-yl)propyl]-4-[2-(4-fluorophenyl)propyl]piperazine;
1-[3-(5-(1,2,4-triazol-1-ylmethyl)-1H-indol-3-yl)propyl]-4-[2-(4-fluorophenyl)propyl]piperazine;
1-[3-(5-(1,2,4-triazol-4-yl)-1H-indol-3-yl)propyl]-4-[2-(3-fluorophenyl)-3-methoxypropyl]piperazine;
1-[3-(5-(1,2,3-triazol-1-yl)-1H-indol-3-yl)propyl]-4-[2-(4-fluorophenyl)propyl]piperazine;
1-[3-(5-(1,2,4-triazol-4-yl)-1H-indol-3-yl)propyl]-4-[2-(3-fluorophenyl)-3,3,3-trifluoropropyl]piperazine;
1-[3-(5-(1,2,4-triazol-4-yl)-1H-indol-3-yl)propyl]-4-(2,2-difluoro-2-phenylethyl)piperazine;
and pharmaceutically acceptable salts thereof.

6. A pharmaceutical composition comprising a compound as claimed in any one of the preceding claims in association with a pharmaceutically acceptable carrier.

7. A process for the preparation of a compound as claimed in claim 1, which comprises:

(A) reacting a compound of formula III with a compound of formula IV:

(III)

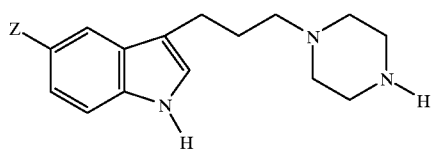

(IV)

$L^1$—A wherein A and Z are as defined in claim 1, and $L^1$ represents a suitable leaving group; or (B) reacting a compound of formula III as defined above with a compound of formula VA or VB respectively:

(VA)

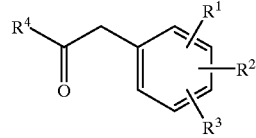

(VB)

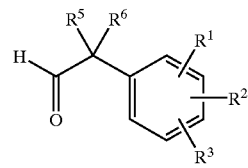

wherein $R^1$, $R^2$, $R^3$, $R^4$, $R^5$ and $R^6$ are as defined in claim 1; in the presence of a reducing agent; or (C) reacting a compound of formula III as defined above with a carboxylic acid derivative of formula VI:

(VI)

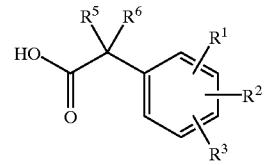

wherein $R^1$, $R^2$, $R^3$, $R^5$ and $R^6$ are as defined in claim 1; in the presence of a condensing agent; followed by treatment with a reducing agent; or (D) reacting a compound of formula VII:

(VII)

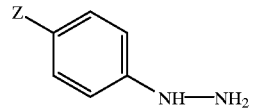

wherein Z is as defined in claim 1; with a compound of formula XII, or a carbonyl-protected form thereof:

(XII)

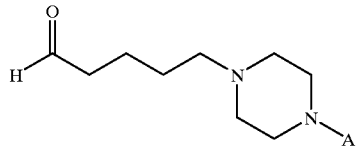

wherein A is as defined in claim 1; or (E) reacting a compound of formula XIV:

(XIV)

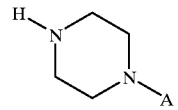

wherein A is as defined in claim 1; with a compound of formula XV:

(XV)

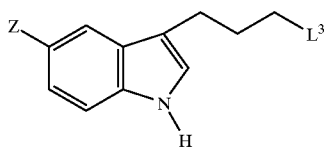

wherein Z is as defined in claim 1, and L³ represents a suitable leaving group; or (F) reducing a compound of formula XVIII:

(XVIII)

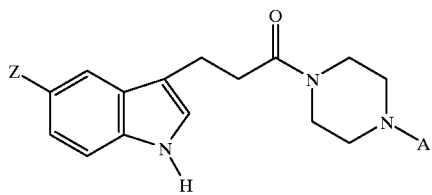

wherein Z and A are as defined in claim 1; or (G) reducing a compound of formula XX:

(XX)

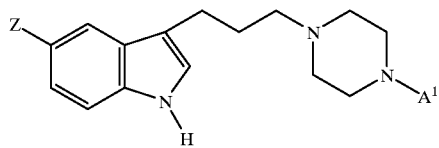

wherein Z is as defined in claim 1, and $A^1$ represents a group of formula (iii) or (iv):

(iii)

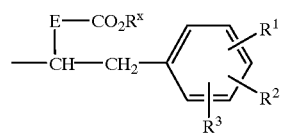

(iv)

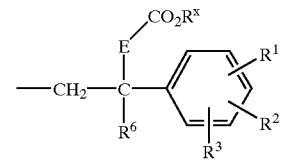

in which E represents a chemical bond or a $C_{1-5}$ alkylene chain, $R^x$ represents $C_{1-6}$ alkyl, and $R^1$, $R^2$, $R^3$ and $R^6$ are as defined in claim 1.

8. A method for the treatment and/or prevention of migraine, cluster headache, chronic paroxysmal hemicrania, headache associated with vascular disorders, tension headache, and paediatric migraine, which method comprises administering to a patient in need of such treatment an effective amount of a compound as claimed in claim 1 or a pharmaceutically acceptable salt thereof.

* * * * *